US007275005B2

(12) United States Patent
Baba et al.

(10) Patent No.: US 7,275,005 B2
(45) Date of Patent: Sep. 25, 2007

(54) WORKED PRODUCT APPEARANCE INSPECTION METHOD AND SYSTEM THEREFORE

(75) Inventors: Susumu Baba, Tokyo-To (JP); Makoto Futami, Tokyo-To (JP); Yuichiro Yotsumoto, Tokyo-To (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 107 days.

(21) Appl. No.: 10/736,976

(22) Filed: Dec. 17, 2003

(65) Prior Publication Data

US 2004/0132297 A1 Jul. 8, 2004

(30) Foreign Application Priority Data

Dec. 18, 2002 (JP) ............................. 2002-367336

(51) Int. Cl.
*G06F 19/00* (2006.01)
*G06K 9/00* (2006.01)

(52) U.S. Cl. ......................................... 702/81; 382/145
(58) Field of Classification Search ................ 702/81, 702/84; 382/275, 311, 149, 145, 147, 151; 356/237.5
See application file for complete search history.

(56) References Cited

U.S. PATENT DOCUMENTS

| | | | | |
|---|---|---|---|---|
| 4,509,075 A * | 4/1985 | Simms et al. ................ | 348/129 |
| 6,047,083 A * | 4/2000 | Mizuno ....................... | 382/141 |
| 6,347,150 B1 * | 2/2002 | Hiroi et al. .................. | 382/149 |
| 6,539,106 B1 * | 3/2003 | Gallarda et al. ............ | 382/149 |
| 6,578,188 B1 * | 6/2003 | Pang et al. .................. | 716/19 |
| 6,580,087 B1 * | 6/2003 | Suzuki et al. ............ | 250/559.4 |
| 6,751,343 B1 * | 6/2004 | Ferrell et al. ................ | 382/145 |
| 6,828,554 B2 * | 12/2004 | Hiroi et al. .................. | 250/307 |
| 6,831,998 B1 * | 12/2004 | Koshishiba et al. ........ | 382/147 |
| 6,900,888 B2 * | 5/2005 | Yoshida et al. ........... | 356/237.4 |
| 6,909,501 B2 * | 6/2005 | Ogawa et al. ............ | 356/237.5 |
| 6,928,185 B2 * | 8/2005 | Yonezawa .................... | 382/149 |
| 6,943,876 B2 * | 9/2005 | Yoshida et al. ........... | 356/237.2 |
| 7,112,791 B2 * | 9/2006 | Nozoe et al. ................ | 250/310 |
| 7,162,071 B2 * | 1/2007 | Hung et al. .................. | 382/144 |
| 2003/0062487 A1 * | 4/2003 | Hiroi et al. .............. | 250/492.2 |

OTHER PUBLICATIONS

Usami et al., Semiconductor Inspection System for Yield Enhancement, 1999, Hitachi Review, vol. 48, No. 6, pp. 354-360.*

* cited by examiner

*Primary Examiner*—John E Barlow, Jr.
*Assistant Examiner*—Toan M. Le
(74) *Attorney, Agent, or Firm*—Oliff & Berridge, PLC (57) ABSTRACT

An inspection system inspects appearances of a plurality of worked products held by a sheet-like inspection target sheet, and includes an image processing station provided at a first location and defect detection stations provided at one or a plurality of second locations away from the first location. The appearance inspection system includes a marking station. The image processing station images each of the worked products held by the inspection target sheet and extracts image-processed data serving as an inspection target. The defect detection station displays on a computer the image-processed data to urge an operator to detect a defect part, and outputs detection result data including position data on the defect part, based on an instruction from the operator. The marking station gives onto the image-processed inspection target sheet a mark representing the defect part, based on the detection result data output by the defect detection station.

8 Claims, 5 Drawing Sheets

WORKED PRODUCT APPEARANCE INSPECTION METHOD AND SYSTEM THEREFORE

BACKGROUND OF THE INVENTION

1. Field of the Invention

The present invention relates to a fine worked product appearance inspection method. More specifically, the present invention relates to a worked product appearance inspection method and a worked product appearance inspection system suitable for the inspection, discrimination, and the like of an appearance of a worked product such as a lead frame for a semiconductor package or a spring member for a hard disk drive (a magnetic disk device) (particularly, a spring member for a suspension having a wiring).

2. Description of Related Art

It is desired to mass-produce fine worked products represented by lead frames for semiconductor packages and spring members for hard disk drives at low apparatus cost while maintaining high quality.

Among these fine worked products, the lead frame for a semiconductor package is, for example, employed as an internal wiring of a semiconductor package. As the high integration of the semiconductor package has recently progressed, a wiring pattern has been increasingly complicated.

The spring member for a hard disk drive (i.e., wiring-added suspension spring member) is employed to be incorporated into a magnetic head suspension which supports a magnetic head that writes and/or reads data to and from a disk. As a hard disk drive has been recently made smaller and thinner in size, the spring member is increasingly made smaller in size. Namely, the magnetic head suspension into which the spring member is incorporated applies a pressing load to a slider that mounts thereon the magnetic head. The distance between disks is narrowed as the hard disk drive is made smaller and thinner. Accordingly, the slider and the magnetic head suspension are made smaller and thinner. Thereby, the spring member for a hard disk drive has been made smaller.

As stated above, when producing the fine worked products such as the lead frame for a semiconductor package or the spring member for a hard disk drive or the like, the individual worked product is increasingly made finer and smaller in size. Further, as the mass-production of the semiconductor packages and the hard disk drives progress, fine worked products employed therefor have been required in large quantities.

Due to this, to manufacture these fine worked products, a method of manufacturing the worked products by etching has been used.

Specifically, when the lead frame for a semiconductor package is manufactured, for example, resist is coated on both sides of a sheet-like workpiece material and the resultant workpiece material is subjected to plate-making and etching, thereby manufacturing a product holding sheet that holds a plurality of lead frames as fine worked products. The product holding sheet is constituted to integrally hold parts of outer peripheries of the plurality of worked products by a frame portion through supporting members, in the view of mass productivity and efficiency. Typically, a predetermined number of worked products are integrated into one frame and a plurality of frames thus integrated are "multiply patterned" on the entire product holding sheet. When producing such a product holding sheet, after the plate-making and the etching, the resist is peeled off from the workpiece material and the workpiece material is washed. The final product holding sheet thus obtained is cut at predetermined positions at need to provide inspection target sheets each having a predetermined size. Appearance of the worked products are inspected per inspection target sheet.

Meanwhile, when the spring member for a hard disk drive is manufactured, a sheet-like workpiece material is subjected to complicated working including a photo-etching step and a plating step, thereby manufacturing a product holding sheet that holds a plurality of spring members as fine worked products. Similarly to the product holding sheet for the lead frames, the product holding sheet thus manufactured is constituted so that a predetermined number of worked products are integrated into one frame and a plurality of frames thus integrated are "multiply patterned" on the entire product holding sheet. Similarly to the product holding sheet for the lead frames, the product holding sheet thus obtained is cut at predetermined positions at need to provide inspection target sheets each having a predetermined size. Appearance of the worked products are inspected per inspection target sheet.

To inspect such worked products, the following inspection method has been conventionally conducted. A series of operations including a plurality of processing necessary for an inspection (e.g., a processing for imaging each worked product and fetching image data, a processing for comparing each fetched image data with basic image data prepared in advance and thereby extracting a defect candidate part under predetermined setting conditions, and a processing for displaying an enlarged image of the extracted defect candidate part and determining whether or not the defect candidate part is really a defect part) are performed per inspection target sheet by one inspection system.

However, when the fine worked products represented by the lead frame for a semiconductor package or the spring member for a hard disk drive are manufactured, the worked products in one inspection target sheet to be inspected are quite large in number and an inspection accuracy requirement is quite strict. Therefore, it disadvantageously takes lots of time to perform the processings necessary for the inspection. In performing the processing for fetching the image data of each worked product, in particular, it is necessary to image the worked product and fetch the image data using an area sensor such as a CCD or the like per inspection target sheet several tens of times. Further, the processing for determining whether or not the defect candidate part really is a defect part requires quite labor. As a result, it takes considerable time to perform the entire processings mainly due to these processings.

To solve these disadvantages, it is possible to simply increase the number of inspection systems that perform the processings necessary for the inspection. When so, however, it is impossible to attain an effect of reducing labor and time proportional to an increase in apparatus cost. As a result, demand for mass productivity and quality improvement cannot be satisfied.

As such a worked product inspection, various inspections such as a visual inspection, an inspection using a loupe, and an inspection using a stereoscope, other than the inspection using the above described inspection apparatus, are performed inside manufactures that manufacture worked products or outside the manufactures (that is, outsourcing). In these circumstances, the apparatus cost, time, and the like for the inspection using the above described inspection apparatus are restricted.

SUMMARY OF THE INVENTION

The present invention has been achieved in light of these respects. It is an object of the present invention to provide a worked product appearance inspection method and a system for the method capable of sufficiently satisfying demands such as mass productivity and high quality of a fine worked product represented by a lead frame for a semiconductor package or a hard disk spring member (a wiring-added suspension spring member, in particular) and holding down apparatus cost.

As a first aspect of the present invention, there is provided a worked product appearance inspection method of inspecting appearance of a plurality of worked products held by a sheet-like inspection target sheet, the method comprising: an image processing step, executed at a first location, of imaging each of the worked products held by the inspection target sheet, and of extracting image-processed data that serves as an inspection target; and a defect detection step, executed at one or a plurality of second locations away from the first location, of displaying on a computer the image-processed data extracted in the image processing step and serving as the inspection target to urge an operator to detect a defect part, and of outputting detection result data including position data on the defect part based on an instruction from the operator.

In the worked product appearance inspection method according to the first aspect of the invention, it is preferable that the image processing step comprises: an image fetching processing step of imaging the each worked product held by the inspection target sheet, and of fetching image data of the each worked product; a defect candidate part extraction processing step of comparing each of the image data fetched in the image fetching processing step with basic image data prepared in advance, and of thereby extracting a defect candidate part under a predetermined setting condition; and an image data extraction processing step of extracting position data and image data on the defect candidate part extracted in the defect candidate part extraction processing step as the image-processed data. It is also preferable that the defect detection step comprises a defect part determination processing step of displaying on the computer an image of the defect candidate part of the each worked product based on the position data and the image data on the defect candidate part extracted in the defect candidate part extraction processing step and the image data extraction processing step of the image processing step to urge an operator to determine the defect part, and of outputting the detection result data including the position data on the defect part based on an instruction from the operator. In this case, it is preferable that exchange of the position data and the image data on the defect candidate part of the each worked product between the first location and the second location is made by either transferring the position data and the image data through a network or by transporting a recording medium that stores the position data and the image data.

Further, in the worked product appearance inspection method according to the first aspect of the invention, the image processing step may comprise an image fetching processing section of imaging the each worked product held by the inspection target sheet, and of extracting the image data as the image-processed data. The defect detection step may also comprise a defect part extraction processing step of displaying on the computer an image of the each worked product based on the image data on the each worked product extracted in the image fetching processing step of the image processing step to urge an operator to extract the defect part, and of outputting the detection result data including the position data on the defect part based on an instruction from the operator. In this case, it is preferable that exchange of the image data on the each worked product between the first location and the second location is made either by transferring the image data through a network or by transporting a recording medium that stores the image data.

Furthermore, the worked product appearance inspection method according to the first aspect of the present invention preferably further comprises a marking step, executed at the first location, of giving onto the inspection target sheet a mark representing the defect part, based on the detection result data output in the defect detection step.

As a second aspect of the invention, there is provided a worked product appearance inspection system of inspecting appearance of a plurality of worked products held by a sheet-like inspection target sheet, the system comprising: an image processing station, provided at a first location, of imaging each of the worked products held by the inspection target sheet, and of extracting image-processed data that serves as an inspection target; and one or a plurality of defect detection stations, provided at one or a plurality of second locations, respectively, away from the first location, of displaying on a computer the image-processed data extracted by the image processing station and serving as the inspection target to urge an operator to detect a defect part, and of outputting detection result data including position data on the defect part based on an instruction from the operator.

It is preferable that the worked product appearance inspection system according to the second aspect of the present invention further comprises; a first data management computer connected to the image processing station, and managing the image-processed data extracted by the image processing station and serving as the inspection target; a second data management computer connected to the one or plurality of defect detection stations, managing the detection result data output by the one or plurality of defect detection stations, and managing the image-processed data extracted by the image processing station and serving as the inspection target; and a network system transferring the image-processed data between the first data management computer and the second data management computer.

Further, in the worked product appearance inspection system according to, the second aspect of the present invention, it is preferable that the image processing station comprises: an image fetching processing section that images the each worked product held by the inspection target sheet, and that fetches the image data; a defect candidate part extraction section that compares each of the image data fetched by the image fetching processing section with basic image data prepared in advance, and that thereby extracts a defect candidate part under a predetermined setting condition; and an image data extraction processing section that extracts position data and image data on the defect candidate part extracted by the defect candidate part extraction processing section as the image-processed data, and that the one or plurality of defect detection stations comprise a defect part determination processing section that displays on the computer an image of the defect candidate part of the each worked product based on the position data and the image data on the defect candidate part extracted by the defect candidate part extraction processing section and the image data extraction processing section of the image processing station to urge an operator to determine the defect part, and that outputs the detection result data including the position data on the defect part based on an instruction from the operator.

Furthermore, in the worked product appearance inspection system according to the second aspect of the present invention, the image processing station may comprise an image fetching processing section that images the each worked product held by the inspection target sheet, and that extracts image data of the each worked product as the image-processed data. The one or plurality of defect detection stations may also comprise a defect part extraction processing section that displays an image of the each worked product on the computer based on the image data on the each worked product extracted by the image fetching processing section of the image processing station to urge an operator to extract the defect part, and that outputs the detection result data including the position data on the defect part based on an instruction from the operator.

Furthermore, the worked product appearance inspection system according to the second aspect of the present invention preferably further comprises a marking station, provided at the first location, of giving onto the inspection target sheet a mark representing the defect part, based on the detection result data output by the one or a plurality of defect detection stations.

Moreover, the worked product appearance inspection system according to the second aspect of the present invention preferably further comprises: a second data management computer connected to the one or plurality of defect detection stations, and managing the detection result data output by the one or plurality of defect detection stations; a control computer connected to the marking station, and controlling the marking station based on the detection result data output by the one or plurality of defect detection stations; and a network system transferring the detection result data between the second data management computer and the control computer.

According to the first and second aspects of the present invention, it is preferable that each worked product held by the inspection target sheet is any one of a lead frame for a semiconductor package and a spring member for hard disk drive.

According to the present invention, the image processing step of imaging the each worked product held by the inspection target sheet and of extracting the image-processed data serving as the inspection target is executed at the first location whereas the defect part detection step of displaying on the computer the image-processed data extracted in the image processing step executed at the first location and serving as the inspection target to urge an operator to detect a defect part, and the defect part detection step of outputting the detection result data including the position data on the defect part based on an instruction from the operator are executed at one or a plurality of second locations, respectively, away from the first location. Therefore, it is possible to execute the defect part detection step (the defect part determination processing or the defect part extraction processing), which is an simple operation but takes lots of time, on the simple computer such as the personal computer. Due to this, the processing apparatus such as the computer and the display, the operator, and the like can be located or secured easily at low cost in accordance with a production volume of the worked products held by the inspection target sheet serving as the inspection target, the processing amount of the inspection target sheet at the first location or the like. Accordingly, it is possible to sufficiently satisfy requirements such as the mass productivity and the high quality of fine worked products and to hold down the apparatus cost.

According to the present invention, the marking step of giving onto the inspection target sheet a mark representing the defect part, based on the detection result data output in the defect detection step executed at the second location is executed at the first location. It is thereby possible to easily discriminate whether or not each worked product held by the inspected inspection target sheet is acceptable.

According to the present invention, the processing performed at the first location is only the image processing step (and the marking step at need). Therefore, these processing steps can be all automatically executed, making it possible to realize efficient appearance inspection processings. In addition, the processings at the second location are performed based only on the image-processed data extracted in the image processing step and the actual inspection target sheet is not physically transported. Therefore, cost, labor, and the like can be effectively reduced.

DETAILED DESCRIPTION OF THE PREFERRED EMBODIMENTS

The embodiments of the present invention will be described hereinafter with reference to the drawings.

Figure 5A:
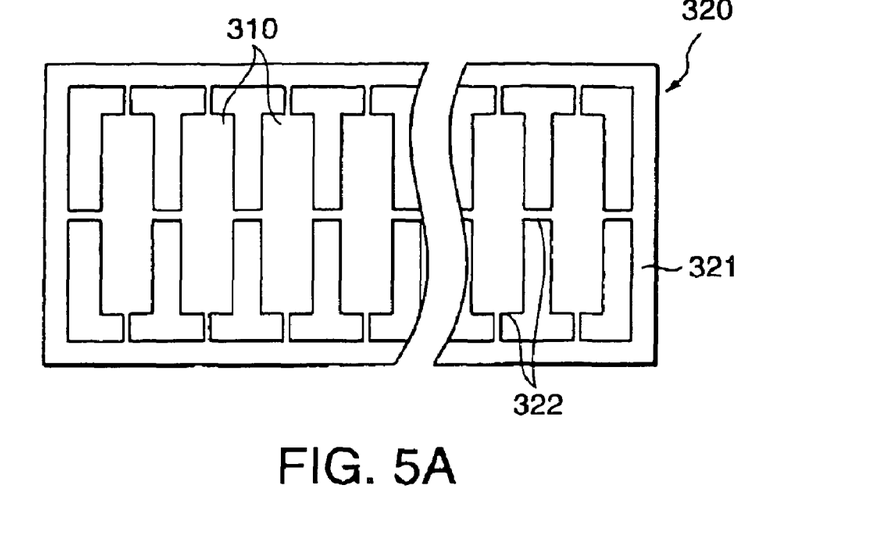
FIGS. 5A and 5B are schematic diagrams which illustrate an example of an inspection target sheet to be inspected by the worked product appearance inspection system shown in FIG. 1.
Figure 5B:
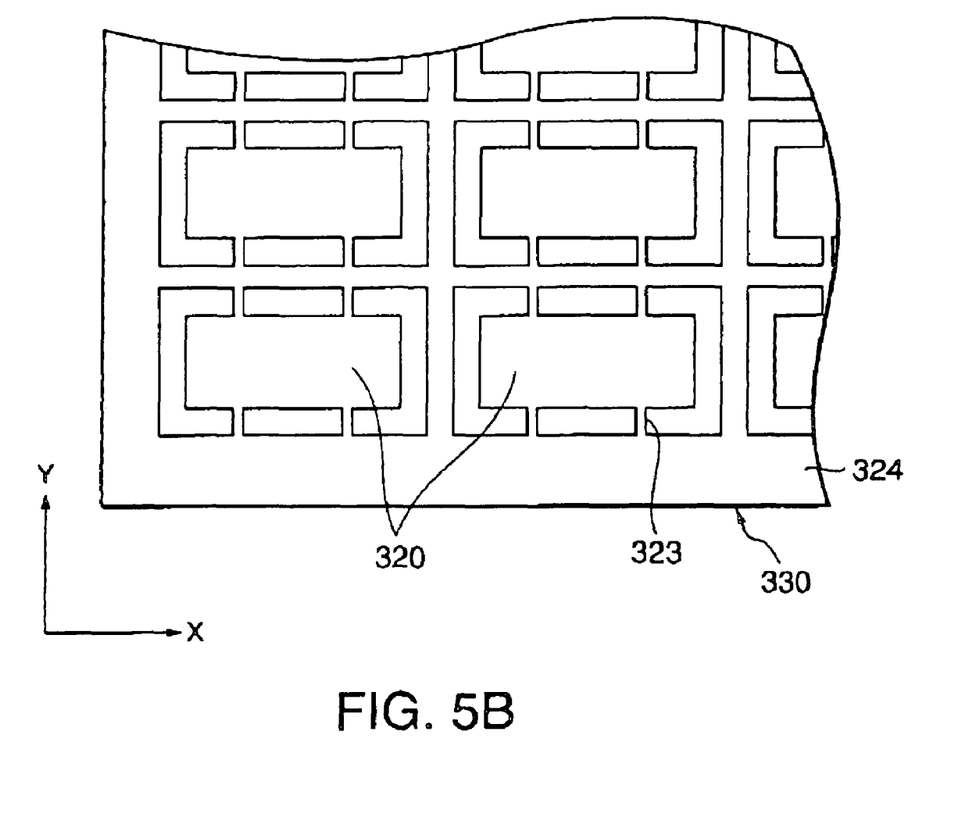

Referring to FIGS. 5A and 5B, an inspection target sheet subjected to an inspection processing and a discrimination processing by a worked product appearance inspection system in an embodiment of the present invention will first be described. In this embodiment, an example of using, as the inspection target sheet, a product holding sheet having parts of outer peripheries of a plurality of worked products integrally held by a frame portion through supporting members will be described.

In FIG. 5A, reference numeral 310 denotes a spring member for a hard disk drive that is a worked product to be subjected to the appearance inspection. The spring member 310 for a hard disk drive herein is a spring member for a wiring-added suspension having a hard disk wiring-added suspension and a flexor provided integrally with each other. As the wiring-added suspension spring member, employed is a member obtained by subjecting a workpiece material (which has copper and stainless steel laminated through a high insulating polyimide resin) (also referred to as "wireless suspension blank") to etching or the like to thereby form a wiring consisting of a copper layer formed on a suspension main body made of stainless steel.

As shown in FIG. 5A, a predetermined number of worked products 310 are connected to a frame portion 321 integrally through supporting portions (joint portions) 322, thereby constituting one frame 320. As shown in FIG. 5B, a predetermined number of frames 320 of this type are arranged in X and Y directions and connected to the frame portion 324 through the supporting portions (joint portions) 323, whereby a product holding sheet 330 is constituted as the inspection target sheet.

The product holding sheet 330 thus constituted is formed by coating resist on both sides of a sheet-like workpiece material and conducting plate-making and etching to the sheet-like workpiece material. The supporting portions 322 of the frame 320 are left without being removed from the workpiece material so as to maintain a connection state between the worked products 310 and the frame portion 321 while the peripheries of the worked products 310 are removed by the etching or the like. Likewise, the supporting portions 323 of the product holding sheet 330 are left without being removed so as to maintain a connection state between the frame 320 and the frame portion 324 while the peripheries of the frame 320 are removed by the etching or the like. It is noted that the configuration of the frame 320 shown in FIG. 5A is only an exemplary one and that the worked products 310 can be connected using bars (not shown) connected integrally with the frame portion 321.

Figure 1:
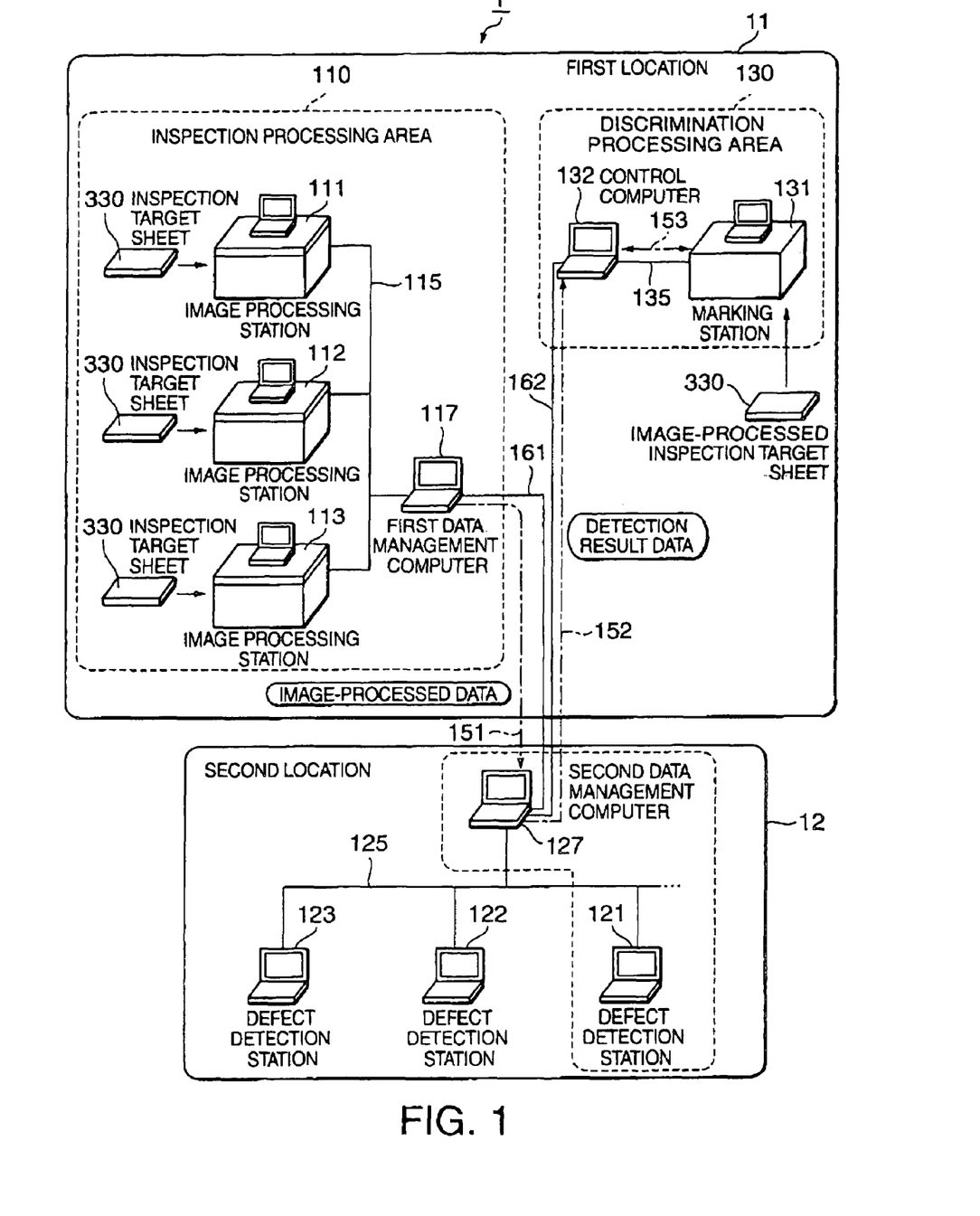
FIG. 1 is a schematic diagram which illustrates the overall configuration of a worked product appearance inspection system in an embodiment of the present invention.

An appearance inspection system 1 which inspects appearance of a plurality of worked products 310 held by the sheet-like inspection target sheet 330 shown in FIGS. 5A and 5B will next be described with reference to FIG.

As shown in FIG. 1, the appearance inspection system 1 inspects appearance of a plurality of worked products (see the members denoted by reference numeral 310 shown in FIG. 5A) held by the sheet-like inspection target sheet 330. The appearance inspection system 1 includes image processing stations 111 to 113 provided at a first location 11 and defect detection stations 121 to 123 provided at a second location 12 away from the first location 11. The appearance inspection system 1 also includes a marking station 131 provided at the first location 11.

Among these constituent elements of the appearance inspection system 1, each of the image processing stations 111 to 113 images each worked product held by the inspection target sheet 330 and extracts image-processed data that serves as an inspection target.

Each of the defect detection stations 121 to 123 displays on a computer the image-processed data serving as the inspection target and extracted by each of the image processing stations 111 to 113 to urge an operator to detect a defect part and outputs detection result data including position data on the defect part based on an instruction from the operator. As the defect detection stations 121 to 123, personal computers or the like can be employed.

The marking station 131 gives onto the image-processed inspection target sheet 330 a mark that represents the defect part, based on the detection result data output from the defect detection stations 121 to 123.

The first location 11 where the image processing stations 111 to 113 and the marking station 131 are provided includes two areas of an inspection processing area 110 and a discrimination processing area 130.

The inspection processing area 110 is provided with a first management computer 117 as well as the image processing stations 111 to 113. The first data management computer 117 is connected to the image processing stations 111 to 113 through a LAN 115 so as to be able to manage the image-processed data serving as the inspection target and extracted by the respective image processing stations 111 to 113. The first data management computer 117 consists of a personal computer or the like.

The discrimination processing area 130 is provided with a control computer 132 as well as the marking station 131. The control computer 132 is connected to the marking station 131 through a LAN 135 so as to be able to control the marking station 131 based on the detection result data output from the defect detection stations 121 to 123. The control computer 132 consists of a personal computer or the like.

The second location 12 where the defect detection stations 121 to 123 are provided is located away from the first location 11. And at the second location 12, a second management computer 127 as well as the defect detection stations 121 to 123 is provided. The second data management computer 127 is connected to the defect detection stations 121 to 123 so as to be able to manage the detection result data output from the defect detection stations 121 to 123 and manage the image-processed data serving as the inspection target and extracted by the image processing stations 111 to 113. The second management computer 127 consists of a personal computer or the like.

In the appearance inspection system constituted as stated above, the first data management computer 117 and the second data management computer 127 are connected to each other through a network system 161 such as a LAN or the Internet or the like so that the image-processed data serving as the inspection target and extracted by the respective image processing stations 111 to 113 can be transferred (see one-dot chain line arrow 151 shown in FIG. 1).

The second data management computer 127 and the control computer 132 are connected to each other through a network system 162 such as a LAN or the Internet or the like so that the detection result data output from the defect detection stations 121 to 123 can be transferred (see one-dot chain line arrow 152 shown in FIG. 1).

The functional configuration of the appearance inspection system 1 shown in FIG. 1 will be described with reference to FIG. 2.

Figure 2:
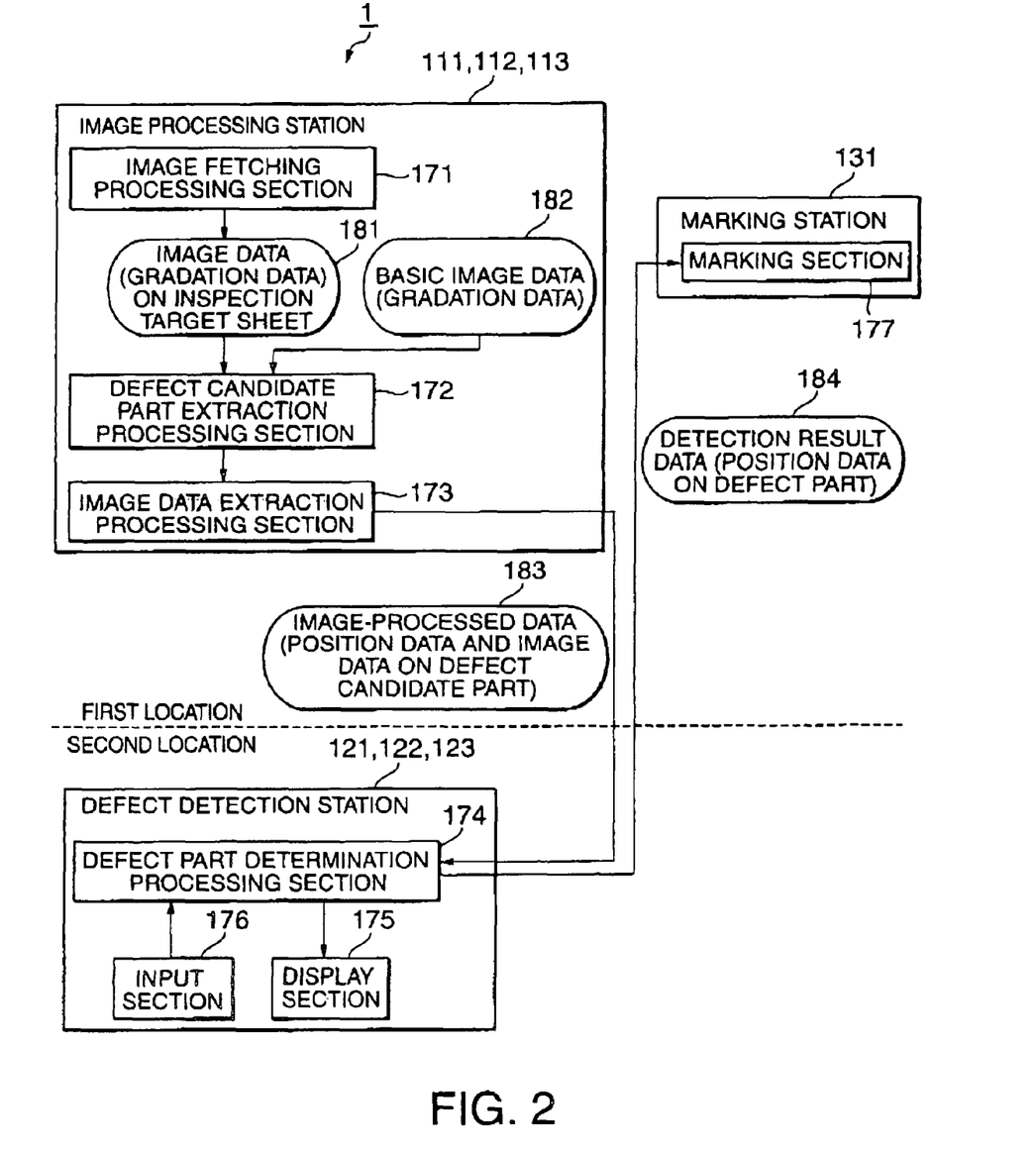
FIG. 2 is a functional block diagram which illustrates the functional configuration of the worked product appearance inspection system shown in FIG. 1.

As shown in FIG. 2, each of the image processing stations 111 to 113 in the appearance inspection system 1 includes: an image fetching processing section 171 that images each worked product held by the inspection target sheet 330 and that fetches the image data; a defect candidate part extraction processing section 172 that compares each image data 181 fetched by the image fetching processing section 171 with basic image data 182 prepared in advance and that extracts a defect candidate part under predetermined setting conditions; and an image data extraction processing section 173 that extracts position data on the defect candidate part extracted by the defect candidate part extraction processing section 172 as image-processed data. The position data and image data on the defect candidate part of each worked product extracted by each of the image processing stations 111 to 113 are associated with each other and managed by the first data managing computer 117.

Each of the defect detection stations 121 to 123 includes a defect part determination processing section 174 that displays an enlarged image of the defect candidate part of each worked product based on the image-processed data 183. The image-processed data 183 includes the position data and image data on the defect candidate part of each worked product extracted by the defect candidate part extraction processing section 172 and the image data extraction processing section 173 of each of the image processing stations 111 to 113. Thus, the defect part determination processing section 174 urges an operator to determine whether or not the defect candidate part is really a defect part and that outputs detection result data 184 including position data on the defect part based on an instruction from the operator. An display section 175 and an input section 176 are connected to the defect part determination processing section 174. By so constituting, an image of the defect candidate part of each worked product obtained by the defect determination processing section 174 is displayed to the operator through the display section 175 and an instruction from the operator input through the input section 176 is input to the defect part determination processing section 174.

The marking station 131 includes a marking section 177 that gives a mark representing the defect part, onto the image-processed corresponding inspection target sheet 330, especially onto the worked product including the defect part (the worked product including at least one defect, the worked product including a predetermined number of defects, or a series of worked products (the frame) including a predetermined number of defect parts), based on the detection result data 184 including the position data on the defect part output from each of the defect detection stations 121 to 123. The marking station 131 is constituted so that a marker can move relatively to the inspection target sheet 330 mounted on a stage in the X and Y directions. Based on the position data on the defect part included in the detection result data 184, the marking station 131 moves the marker up to a predetermined position on the inspection target sheet 330 and thereby gives the mark.

In the appearance inspection system 1 thus constituted, the image-processed data 183 including the position data and image data on the defect candidate part of each worked product extracted by each of the image processing stations 111 to 113 is transferred through the network system 161 between the first data management computer 117 and the second data management computer 127 (see FIG. 1). The detection result data 184 including the position data on the defect part output from each of the defect detection stations 121 to 123 is transferred through the network system 162 between the second data management computer 127 and the control computer 132 (see FIG. 1).

Figure 3:
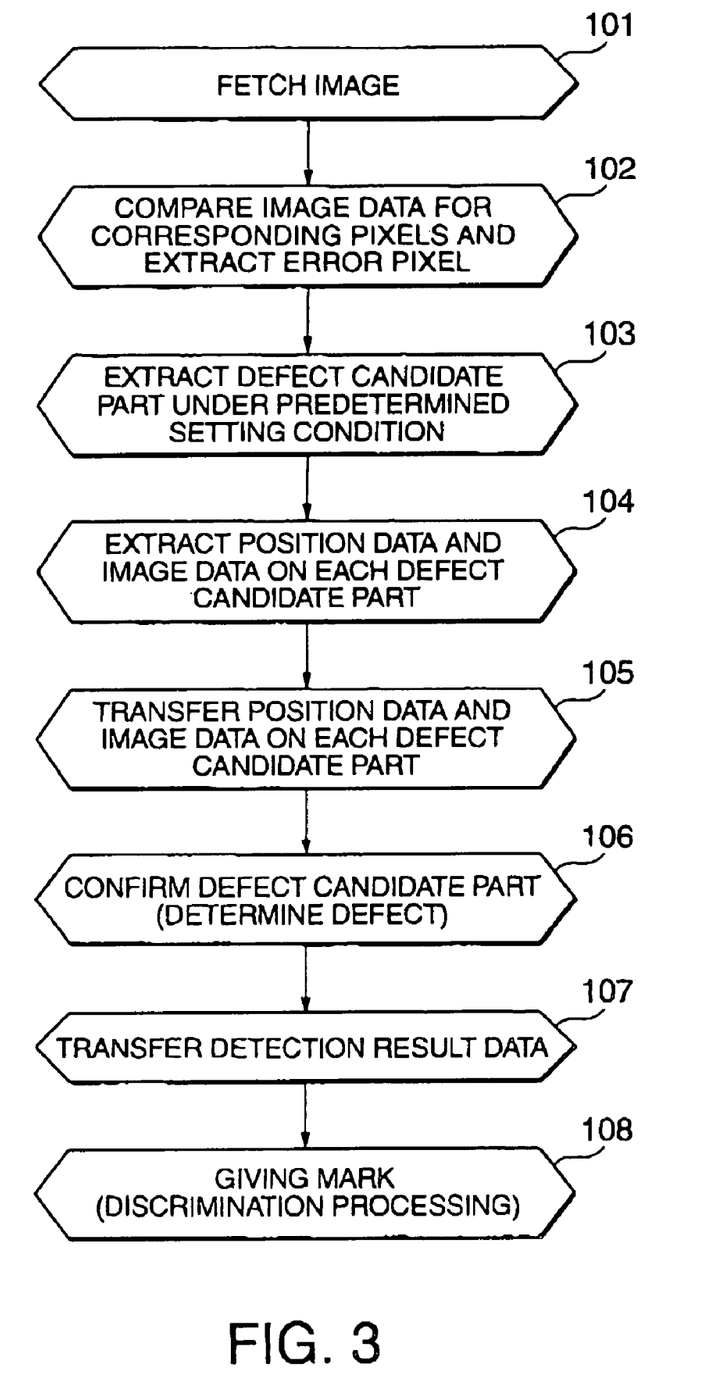
FIG. 3 is a processing flow chart for explaining an inspection processing and a discrimination processing performed by the worked product appearance inspection system shown in FIG. 1.

An inspection processing and a discrimination processing performed by the appearance inspection system 1 shown in FIGS. 1 and 2 will be described with reference to FIG. 3.

The inspection target sheet 330 shown in FIGS. 5A and 5B is prepared and input to each of the image processing stations 111 to 113 provided in the inspection processing area 110 at the first location 11.

Each of the image processing stations 111 to 113 images an entire inspection area of the inspection target sheet 330 using a CCD (an area sensor) as the image fetching processing section 171 (step S101). An example in which the inspection area of the inspection target sheet 330 is a square having a length of 350 millimeters in each of the X and Y directions will be described herein. Each of the image processing stations 111 to 113 images the inspection area of the inspection target sheet 330 while feeding the inspection area at predetermined pitches in the X and Y directions corresponding to an imaging area of the CCD and thereby obtains the image of the entire inspection area. In this step, it is necessary to fetch the image of the inspection target sheet 330 at a high resolution so as to satisfy a requirement for the accuracy and quality of the worked product. Specifically, it is preferable to use 1,000×1,000 pixels, i.e., one million pixels as pixels of the CCD. In this case, when the imaging area of the CCD is about seven millimeters by seven millimeters, the number of imaging times is 2,500 and the entire image can be obtained by collecting 2,500 images. The image data on each image is obtained as gradation data having, for example, 256 gradations.

The defect candidate part extraction processing section 172 compares the image data corresponding to each image fetched by the image fetching processing section 171 with the corresponding basic image data prepared in advance per pixel and extracts a pixel having a large gradation difference as an error pixel (step S102). In this comparison, the defect candidate part extraction processing section 172 calculates a difference in gradation between the corresponding pixels of both the image data and the basic image data, compares the calculated difference thus obtained with a predetermined threshold, and finally determines that each pixel the difference of which is greater than the threshold as the error pixel.

As the basic image data, image data on a good inspection target sheet imaged similarly to the above, or the image data on an appropriate one of the images of the inspection target sheet serving as the inspection target can be used. Typically, in the case that the inspection target sheet includes worked products arranged repeatedly as shown in FIGS. 5A and 5B, several different images, each obtained by one imaging operation, are sufficient to prepare for the inspection target sheet; thus, the images obtained by the imaging operations performed 2500 times can be satisfactorily compared with the basic image data thus prepared.

Thereafter, the defect candidate part extraction processing section 172 extracts the defect candidate part, based on the error pixels obtained in step S102, under the setting conditions for extracting the defect candidate. The setting conditions include continuity of error pixels, and the number of error pixels in a predetermined pixel area about each pixel (step S103). The image processing data extraction section 173 extracts position data and image data on the defect candidate part extracted in step S103 (step S104). To extract the position data and the image data, it is the simplest to do so per image obtained by one imaging operation. However, the present invention is not limited to this extraction method. The position data and the image data may be extracted in, for example, a predetermined range including the position of the defect candidate part within the image obtained by one imaging operation.

By comparing the image data corresponding to all the images with the basic data, the image-processed data 183 that includes the position data and the image data on all the defect candidate parts can be extracted. The image-processed data 183 thus extracted is managed by the first data management computer 117.

The image-processed data 183 that includes the position data and the image data thus extracted on all the defect candidate parts is transferred from the first data management computer 117 to the second data management computer 127 provided at the second location 12 through the network system 161 (step S105).

At the second location 12, the image-processed data 183 thus transferred is fed from the second data management computer 127 to each of the defect detection stations 121 to 123 through the LAN 125. In each of the defect detection stations 121 to 123, the defect part determination processing section 174 displays on the display section 175 an enlarged image of the defect candidate part of each worked product based on the image-processed data 183 thus fed to urge an operator to visually determine whether or not the defect candidate part is really a defect part (confirmation of a defect candidate part), and outputs the detection result data 184 including the position data on the defect part based on an instruction from the operator input through the input section 176 (step S106). In this step, when a plurality of defect detection stations 121 to 123 are provided, the defect detection step (defect part determination step) is distributed to the defect detection stations 121 to 123. Therefore, the image-processed data 183 is divided by the number of inspection target sheets 330 or by the number of partial area units in each inspection target sheet 330 and pieces of the divided image-processed data are fed to the respective defect detection stations 121 to 123.

When the defect detection processing of each of the defect detection stations 121 to 123 is finished, the detection result data 184 that includes the position data on all the defect parts output from the defect detection stations 121 to 123 is fed to the second data management computer 127 through the LAN 125. The detection result data 184 thus output is managed by the second data management computer 127.

The second data management computer 127 transfers the detection result data 14 that includes the position data on all the defect parts and thus managed by the computer 127 to the control computer 132 provided in the discrimination processing area 132 at the first location 11 through the network 162 (step 107).

In the discrimination processing area 130 at the first location 11, the detection result data 184 thus transferred is fed from the control computer 132 to the marking station 131. In the marking station 131, the marking section 177 gives a mark onto the image-processed corresponding inspection target sheet 330, especially onto the worked product or frame including the defect part, per worked product (denoted by reference symbol 310 shown in FIG. 5A) or per frame (denoted by reference symbol 320 shown in FIGS. 5A and 5B), based on the detection result data 184 thus fed (step S108). It is thereby possible to easily discriminate whether or not each worked product 310 held by the inspected inspection target sheet 330 is acceptable. As the marking, a color is given to the inspection target sheet, or a slight concave portion is formed in the inspection target sheet. However, the marking method is not limited to these methods.

By performing the processings in steps 101 to 108, the appearance inspection system 1 completes the inspection processing and the discrimination processing to the inspection target sheet 330.

Further Embodiment

The embodiment stated above are given only for exemplary and the present invention is not limited to the embodiment.

Specifically, in the embodiment stated above, the image-processed data (the position data and the image data on the defect candidate part of each worked product) 183 is exchanged between the first location 11 and the second location 12 by transferring the image-processed data 183 between the first data management computer 117 and the second data management computer 127. However, the present invention is not limited to the embodiment and the data exchange can be made by transporting the recording medium (such as the SDLT, the HDD, or the floppy® disk) that stores the image-processed data 183.

In the embodiment stated above, all the processing sections (the image fetching processing section 171, the defect candidate part extraction processing section 172, and the image data extraction processing section 173) in each of the image processing sections 111 to 113 are constituted integrally as one apparatus. However, the present invention is not limited to the embodiment. The image fetching processing section 171, the defect candidate part extraction processing section 172, and the image data extraction processing section 173 may be constituted as separate apparatuses.

Figure 4:
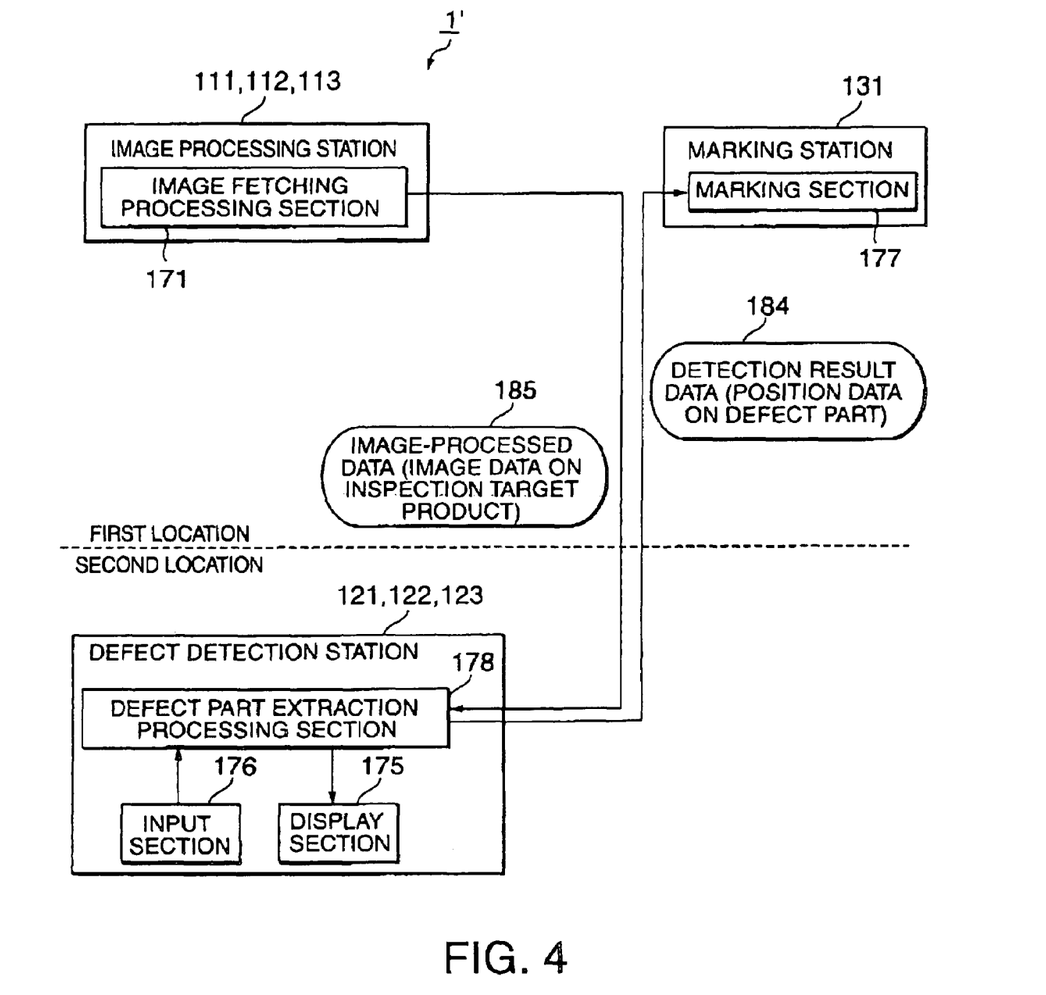
FIG. 4 is a functional block diagram which illustrates the functional configuration of a worked product appearance inspection system in another embodiment of the present invention.

Furthermore, it is possible to provide a worked product appearance inspection system 1' as shown in FIG. 4, as another embodiment of the present invention.

As shown in FIG. 4, the appearance inspection system 1' in this embodiment differs from the appearance inspection system 1 shown in FIG. 2 in that the configurations of the image processing stations 111 to 113 and the defect detection stations 121 to 123 are changed. The appearance inspection system 1' shown in FIG. 4 is substantially equal in configuration to the appearance inspection system 1 shown in FIG. 2 except for the image processing stations 111 to 113 and the defect detection stations 121 to 123. In the appearance inspection system 1' shown in FIG. 4, the same constituent elements as those of the appearance inspection system 1 shown in FIG. 2 are denoted by the same reference symbols, respectively, and will not be described herein in detail.

Specifically, in FIG. 4, each of the image processing stations 111 to 113 includes the image fetching processing section 171 that images each worked product held by the inspection target sheet 330 and that extracts image data as the image-processed data 185. Each of the defect detection stations 121 to 123 includes a defect part extraction processing section 178 that displays the image of each worked product based on the image-processed data 185 including the image data on each worked product extracted by the image fetching processing section 171 to urge an operator to extract the defect part and that outputs the detection result data 184 that includes the position data on all the defect parts based on an instruction from the operator.

In the appearance inspection system 1' constituted as stated above, the exchange of the image-processed data (image data on each worked product) 185 between the first data management computer 117 and the second data management computer 127 can be made by transferring the image-processed data (image data on each worked product) 185 between the first data management computer 117 and the second data management computer 127 through the network 161 or by transporting a recording medium (such as an SDLT, a HDD, or a floppy® disk) that stores the image-processed data (image data on each worked product) 185.

Incidentally, in the embodiment stated above with respect to FIGS. 1 to 4, the area sensor such as the CCD or the like is employed as an imaging device used in the image fetching processing section 171 of each of the image processing stations 111 to 113. However, the imaging device is not limited to the area sensor but a simpler imaging device such as a commercially available scanner or digital camera or the like may be used.

In the embodiment stated above with respect to FIGS. 1 to 4, the three defect detection stations 121 to 123 are provided at the second location 12. However, the minimum configuration necessary for the defect part detection step (defect part determination processing) is the configuration indicated by a dotted line in FIG. 1 (one defect detection station 121 and the second data management computer 127). When a processing quantity is small at the second location 12, only one defect detection station 121 may be provided. Conversely, when the processing quantity is large at the second location 12, more than three defect detection stations may be provided.

In the embodiment stated above with respect to FIGS. 1 to 4, the second location 12 is concentrated in one portion.

However, the present invention is not limited to the embodiment but the second location 12 may be provided to be distributed to a plurality of portions.

In the embodiment stated above, the example in which each worked products held by the inspection target sheet 330 is the wiring-added suspension spring member for a hard disk drive has been described. However, the present invention is not limited to this example but is similarly applicable to the inspection target sheet that holds arbitrary fine worked products such as a lead frame for a semiconductor package.

What is claimed is:

1. A method for inspecting an appearance of a plurality of worked products held by an inspection target sheet, the method comprising:
    conducting image processing at a first location to obtain image-processed data; and
    conducting defect detection at a second location remote from the first location using the image-processed data obtained during image processing;
    wherein:
    conducting image processing comprises:
        imaging each worked product held by the inspection target sheet to obtain image data;
        retrieving the image data relating to each worked product;
        comparing the retrieved image data with basic image data prepared in advance of image processing to identify a defect candidate part based on a predetermined condition; and
        extracting position data and image data relating to the defect candidate part as image-processed data;
    conducting defect detection comprises:
        displaying an image of the defect candidate part based on the image-processed data to urge an operator to determine whether the defect candidate part is a defect part; and
        creating detection result data including position data for each defect part based on the operator's determination and the image-processed data; and
    wherein:
    each of the plurality of worked products is either a lead frame for a semiconductor package or a spring member for a hard disk drive.

2. The method according to claim 1, wherein the image-processed data is transferred from the first location to the second location through a network.

3. The method according to claim 1, wherein the image-processed data is transferred from the first location to the second location by transporting a recording medium on which the image-processed data is stored.

4. The method according to claim 1, further comprising conducting marking at the first location, wherein conducting marking comprises marking the inspection target sheet to identify the defect part based on the detection result data.

5. A system for inspecting an appearance of a plurality of worked products held by an inspection target sheet, the system comprising:
    an image processing station, provided at a first location, for producing image-processed data; and
    a defect detection station, provided at a second location remote from the first location, for detecting defect parts using the image-processed data produced by the image processing station;
    wherein:
    the image processing station comprises:
        an image retrieving processing section that images each worked product held by the inspection target sheet and retrieves image data relating to each worked product;
        a defect candidate part extraction section that compares the retrieved image data with basic image data prepared in advance to identify a defect candidate part based on a predetermined condition; and
        an image data extraction processing section that extracts position data and image data relating to the defect candidate part as image-processed data;
    the defect detection station comprises a defect part determination processing section that displays an image of the defect candidate part based on the image-processed data to urge an operator to determine whether the defect candidate part is a defect part, and that creates detection result data including position data for the defect part based on the operator's determination and the image-processed data; and
    wherein:
    each of the plurality of worked products is either a lead frame for a semiconductor package or a spring member for a hard disk drive.

6. The system according to claim 5, further comprising:
    a first data management computer connected to the image processing station that manages the image-processed data;
    a second data management computer connected to the defect detection station that manages the detection result data; and
    a network system that transfers the image-processed data from the first data management computer to the second data management computer.

7. The system according to claim 5, further comprising a marking station, provided at the first location, that marks the inspection target sheet to identify the defect part based on the detection result data.

8. The system according to claim 7, further comprising:
    a second data management computer connected to the defect detection station that manages the detection result data;
    a control computer connected to the marking station that controls the marking station based on the detection result data; and
    a network system that transfers the detection result data from the second data management computer to the control computer.

* * * * *